United States Patent [19]

Oono et al.

[11] Patent Number: 4,588,822

[45] Date of Patent: May 13, 1986

[54] PHYSIOLOGICALLY ACTIVE SUBSTANCES SS 12538, THEIR PREPARATION AND A NOVEL MICROORGANISM PRODUCING SAME

[75] Inventors: Junji Oono, Narita; Kenichi Yano, Chiba; Junichi Sato, Narashino; Tadayuki Kouda, Narita; Yoichiro Ogawa, Chiba; Kouichi Yokoi, Kashiwa; Toshiaki Nakashima, Shisuimachi, all of Japan

[73] Assignee: SS Pharmaceutical Co., Ltd., Tokyo, Japan

[21] Appl. No.: 482,409

[22] Filed: Apr. 6, 1983

[30] Foreign Application Priority Data

Apr. 7, 1982 [JP] Japan .............................. 57-57790
Jun. 18, 1982 [JP] Japan .............................. 57-104899
Aug. 31, 1982 [JP] Japan .............................. 57-151496

[51] Int. Cl.$^4$ ............................................. C07D 309/32
[52] U.S. Cl. .................................. 549/417; 435/125; 435/253
[58] Field of Search ........................ 549/417; 514/460

[56] References Cited

U.S. PATENT DOCUMENTS 4,219,483  8/1980  Kuhla et al. ........................ 549/417

*Primary Examiner*—Nicky Chan
*Attorney, Agent, or Firm*—Oblon, Fisher, Spivak, McClelland & Maier

[57] ABSTRACT

Disclosed are novel physiologically active substance SS 12538, process for its preparation and a novel microorganism producing the same.

The novel physiologically active substance SS 12538 is represented by the following formula (I):

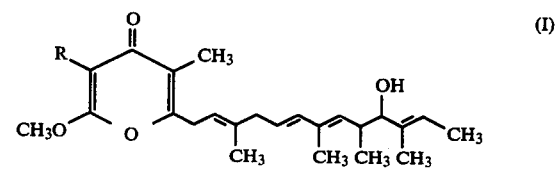

in which R represents a hydrogen atom, a methyl group or an ethyl group.

SS 12538 is obtained by inoculating a novel strain S 12538 in a nutrient-containing medium and cultivating aerobically.

SS 12538 has excellent vasodilating action and antibiotic action against a certain gram positive bacteria and dermatophytes.

4 Claims, 10 Drawing Figures

( X 14000 )

PHYSIOLOGICALLY ACTIVE SUBSTANCES SS 12538, THEIR PREPARATION AND A NOVEL MICROORGANISM PRODUCING SAME

BACKGROUND OF THE INVENTION

Field of the Invention

This invention relates to novel physiologically active substances SS 12538, a process for producing the substances, and a novel microorganism producing the substances.

SUMMARY OF THE INVENTION

We isolated a great number of microorganism from natural soils and made the extensive studies on their products. As a result, it was found that a strain S 12538 isolated from a soil sample collected at Satsukigaoka, Chiba Prefecture, Japan was a novel microorganism which was able to produce novel physiologically active substances SS 12538 of the following formula (I)

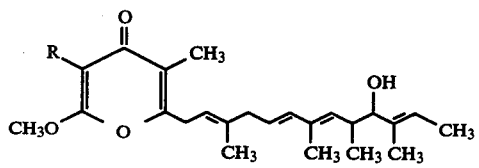

in which R represents a hydrogen atom, a methyl group or an ethyl group. The substances were found to have excellent vasodilating action and the antibiotic action against a certain gram positive bacteria and denmatophytes. The present invention has been accomplished on the basis of the above findings.

Accordingly, an object of the invention is to provide novel physiologically active substances SS 12538, their preparation and a novel microorganism which produces the same.

DETAILED DESCRIPTION OF THE INVENTION AND PREFERRED EMBODIMENTS

Figure 1:
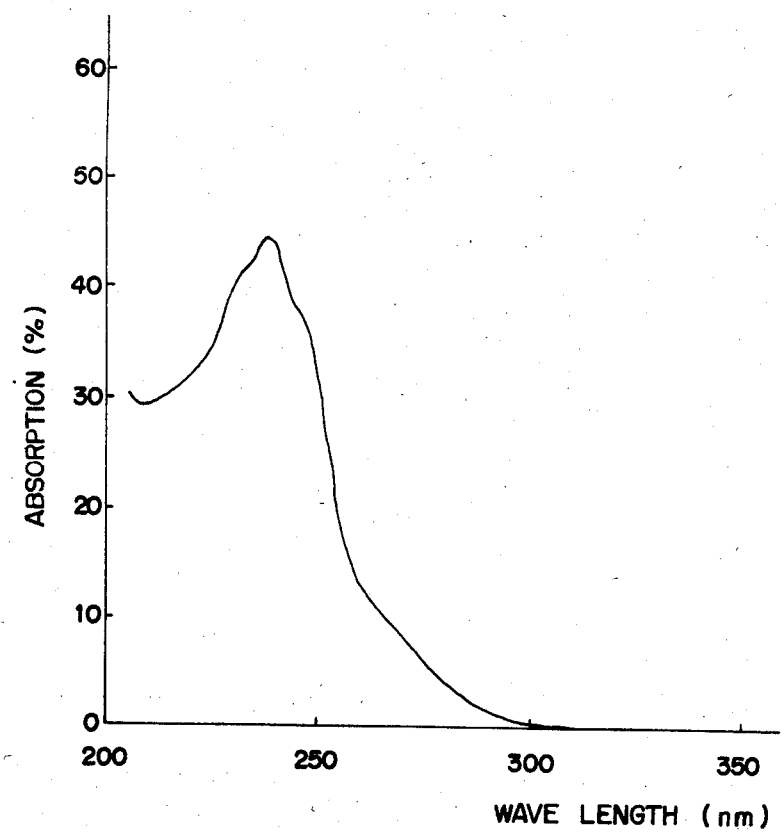
FIG. 1 is an UV absorption spectrum (solvent: methanol) of physiologically active substance SS 12538A of the present invention.

A strain capable of producing the physiologically active substances SS 12538 according to the present invention have the following characteristics.

1. Morphology

Sporulation mycelia simply branch from aerial mycelia with their tip portion being spiral in form. No whirls are recognized. Ten or more matured conidia link together with spores having a short cylindrical-ellipsoidal form and a size of 0.5–0.8 × 0.8–1.5 μm. The spores have a hairy surface. Neither of sporangia, flagellous spores or sclerotia are found. Fragmentation of substrate mycelium is not recognized.

2. Growth Characteristics on Various Media (cultured at 27° C. for 14 days)

| Medium | Growth | Aerial Mycelium | | color of Reverse Substrate Mycelium | Soluble Pigment |
|---|---|---|---|---|---|
| | | Formation | Color | | |
| Sucrose-nitrate-agar | poor | thin scant | light brownish gray | colorless | none |
| Glucose-asparagine-agar | good | thin scant | white-light gray | pale yellow | none |
| Glycerine-asparagine-agar | good | thin scant | white-light bluish gray | dull yellowish orange | none |
| Starch-inorganic salt-agar | good | good | medium gray | dull yellowish orange | faint, yellowish brown |
| Tyrosine-agar | good | good | white-light gray | brownish olive | none |
| Nutrient agar | good | not formed | — | pale yellow | none |
| Yeast extract-malt extract-agar | good | fairly good | white-light bluish gray | light yellowish brown | none |
| Oat meal-agar | good | good | medium gray | pale yellow | none |

| Medium | Growth | Aerial Mycelium Formation | Aerial Mycelium Color | color of Reverse Substrate Mycelium | Soluble Pigment |
|---|---|---|---|---|---|
| Glycerine-nitrate-agar | good | thin scant | yellowish white | pale yellow | none |
| Calcium malate agar | poor | thin scant | light brownish gray | colorless | none |

(Note)
The names of colors indicated are determined according to "Concise Manual of Color Names" (Japan Color Investigation K.K. 1981).

3. Physiological Characteristics (1) Temperature range for growth:
  Possible growth temperature    16–39° C.
  Optimum growth temperature    26–35° C.
(2) Liquefaction of gelatin    Positive
(3) Hydrolysis of starch    Positive
(4) Coagulation of skim milk    Positive
(5) Peptization of skim milk    Positive
(6) Formation of melanoid pigment    Negative
(7) Reduction of nitrate    Positive
(8) Decomposition of cellulose    Negative
(9) Utilization of carbon sources
  D-Glucose    +
  L-Arabinose    −
  Sucrose    −
  D-Xylose    −
  L-Inositol    −
  D-Mannitol    −
  D-Fructose    −
  Rhamnose    −
  Raffinose    +
  Cellulose    −
  Galactose    +
  Salicin    −
  Lactose    +
  D-Sorbitol    +
  D-Mannose    +
  Inulin    −

(Note)
+: Utilized
−: Not utilized

In view of the above characteristics and presence of L-diaminopimelic acid as a composition of cell wall, it will be apparent that the strain S 12538 belongs to the genus Streptomyces. When the mycological characteristics of the strain are referred to "The Actinomycetes", Vol. 2 (1961) by Waxman, ISP report "International Journal of Systematic bacteriology", Vol 18, pages 69 and 279 (1968), by Shirling and Gotlieb, the ISP report Vol. 19, page 391 (1969) and Vol. 22, page 265 (1972), and "Bergey's Manual of Determinative Bacteriology" eighth edition (1974), strains of the type in which aerial mycelia have a gray color series, spore chains are spiral, a spore surface structure is hairy, no melanoid pigment is produced, and a range of utilization of carbon sources is narrow as in the present strain S 12538 include *Streptomyces karnatakensis* and *Streptomyces pactum*. The results of comparing these two strains with strain S 12538 are shown in the following table.

|  | S 12538 | *Streptomyces pactum* ISP 5530 | *Streptomyces karnatakensis* ISP 5345 |
|---|---|---|---|
| Form of *aerial mycelia* | spiral | spiral | spiral |
| Spore surface | hairy | hairy | hairy |
| Color of *aerial mycelia* | white-light bluish gray-light gray-medium gray | white-light bluish gray-light gray | white-light bluish gray-bluish gray |
| Color of Reverse substrate mycelium | colorless-pale yellow-light yellowish brown | colorless-light yellowish brown-grayish brown | colorless-pale yellow-light yellowish brown |
| Soluble pigment | scarcely contained | taint yellowish brown | taint yellowish brown |
| Melanoid pigment | | | |
| trypton.yeast broth | − | − | − |
| peptone.yeast iron agar | − | − | − |
| tyrosine agar | − | − | − |
| Hydrolysis of starch | + | + | + |
| Coagulation of skim milk | + | + | + |
| Peptization of skim milk | + | + | + |
| Liquefaction of gelatin | + | + | + |
| Reduction of nitrate | + | − | − |
| Utilization of carbon sources | | | |
| D-Glucose | + | + | + |
| L-Arabinose | − | − | − |

|  | S 12538 | *Streptomyces pactum* ISP 5530 | *Streptomyces karnatakensis* ISP 5345 |
| --- | --- | --- | --- |
| Sucrose | − | − | − |
| D-Xylose | − | − | − |
| L-Inositol | − | − | − |
| D-Mannitol | − | − | − |
| D-Fructose | − | − | − |
| Rhamnose | − | − | − |
| Raffinose | + | − | − |
| Cellulose | − | − | − |
| Galactose | + | + | + |
| Salicin | − | − | − |

As will be seen from the above table, the strain S 12538 is greatly different from *Streptomyces karnatakensis* ISP 5345 with respect to the color of aerial mycelia, reduction of nitrate and the utilization of raffinose. On the other hand, the present strain is different from *Streptomyces pactum* ISP 5530 with respect to the reduction of nitrate and the utilization of raffinose but are almost similar in mycological characteristics. Accordingly, S 12538 strain was identified as a strain of *Streptomyces pactum*.

In order to distinguish the present S 12538 strain from the known strain, we designated it as *Streptomyces pactum* S 12538 and deposited it to the Fermentation Research Institute as an Inter National Deposition at Deposit No. FERM BP-265.

Physiologically active substances SS 12538 of the present invention can be prepared by inoculating the above strain in a nutrient-containing medium and cultivating aerobically.

As a matter of course, all strains including not only the above strain, but also artificial and natural mutants or variants can be used for the preparation of the substances SS 12538.

Media used for the cultivation may be synthetic media, semi-synthetic media and natural media provided that they contain nutrients which the bacteria can utilize.

Among nutrients in media, carbon sources are, for example, glucose, glycerol, dextrin, starch, wheator, molasses, soybean oil or mixtures thereof. Nitrogen sources are, for example, soybean flour, wheat germ, meat extract, peptone, dry yeast, cotton seed meal, fish meal, corn steep liquor, ammonium sulfate, sodium nitrate and mixtures thereof.

If necessary, inorganic salts such as calcium carbonate, sodium chloride, phosphates and the like are added to promote growth of bacteria, facilitating production of substances SS 12538. Also, organic matters, inorganic matters and ordinary antifoamer such as silicone oils or Adecanol (commercial name) may be added.

The cultivation is effected by liquid culture and particularly by deep culture as in the production of ordinary antibiotics. The cultivation is conducted under aerobic conditions and suitable temperatures for the cultivation range from 23° to 30° C. and, in most cases, the cultivation is effected in the vicinity of 27° C. Physiologically active substances SS 12538 reach a maximum in amount for 2–7 days when produced either by shaking culture or by deep culture.

The resulting culture product contains a mixture of physiologically active substance SS 12538A of the formula (I) in which R represents methyl, SS 12538B of the formula in which R represents hydrogen and SS 12538C of the formula in which R represents ethyl. In order to isolate these substances from one another, various techniques should properly be used in combination in consideration of physico-chemical properties of these substances SS 12538A, SS 12538B and SS 12538C as particularly described in examples appearing hereinafter.

That is, these physiologically active substances are usually present in mycelia and a culture filtrate. Accordingly, the mycelia are separated from the culture broth by centrifugal separation or filtration. The mycelia and culture filtrate are subjected to ordinary separation techniques used in combination such as solvent extraction, precipitation, ion exchange resin technique, gel filtration, adsorption or distribution chromatography and dialysis thereby isolating and purifying physiologically active substances SS 12538.

One of preferable isolation and purification techniques is described below.

That is, a culture broth is separated into mycelia and broth supernatant by centrifugation or the like. Then, the wet mycelia cake and the broth supernatant are, respectively, extracted with, for example, methanol, ethyl acetate or the like. The solvent extract from the wet mycelia cake and the broth supernatant are combined together, followed by distilling off the solvent. The resulting residue is dissolved in a small amount of water and extracted with ethyl acetate several times, followed by evaporating to dryness under reduced pressure to obtain a dark brown oily substance. This oily substance is subjected to an adsorption chromatography using silica gel. By the silica gel chromatography, a fraction containing SS 12538C first elutes followed by elution of a fraction containing SS 12538A and a fraction containing SS 12538B in this order. These active fractions are, respectively, collected and concentrated under reduced pressure, by which SS 12538A, SS 12538B and SS 12538C are, respectively, isolated in the form of colorless oils.

The thus isolated physiologically active substances SS 12538 have the following physico-chemical and biological properties.

I. SS 12538A

1. Physico-chemical Properties (1) Color and nature of substance: Colorless oil (2) Molecular weight (determined by mass spectrum of an acetate of SS 12538A) 400

(3) Thin layer chromatography

Carrier: silica gel plate $F_{254}$ (Merck Inc.)

| Developing Solvent Systems | Rf Values |
| --- | --- |
| Chloroform/methanol (100:1) | 0.42 |
| Benzene/ethyl acetate (1:1) | 0.33 |

| Developing Solvent Systems | Rf Values |
|---|---|
| Benzene/acetone (10:3) | 0.31 | an instantaneous pulse meter from RR intervals of an electrocardiogram. Each parameter was recorded on a polygraph. Changes of these parameters prior to and after administration of each compound were observed. The results are shown in Table 1.

TABLE 1

| Compounds | Dose (μg/kg) | Coronary Blood Flow | | Blood Pressure | | Heart Rate |
|---|---|---|---|---|---|---|
| | | Increase (%) | Duration (min) | Reduction (%) | Duration (min) | Reduction (%) |
| SS 12538A | 3 | 17.1 | 10 | 4.9 | 7 | 2.3 |
| | 10 | 168.6 | 20 | 12.6 | 10 | 2.9 |
| | 30 | 441.3 | 40 | 28.7 | 30 | 1.8 |
| Di-pyridamol | 300 | 135.7 | 20 | 13.2 | 16 | 0 |

(4) Color reactions

The substance presents yellow color with 2,4-dinitrophenylhydrazine reagent and dark purple color with anisaldehyde-sulfuric acid. No characteristic colors are obtained with ferric chloride solution.

(5) Solubilities in Solvents

Soluble in chloroform, ethyl acetate, acetone, ethyl ether, ethanol, methanol, pyridine, benzene and dimethyl sulfoxide but sparingly soluble in water.

(6) UV absorption spectrum $\lambda_{max}^{MeOH} 239$ E$_1$ $cm^{1\%} 845$ (FIG. 1).

Figure 2:
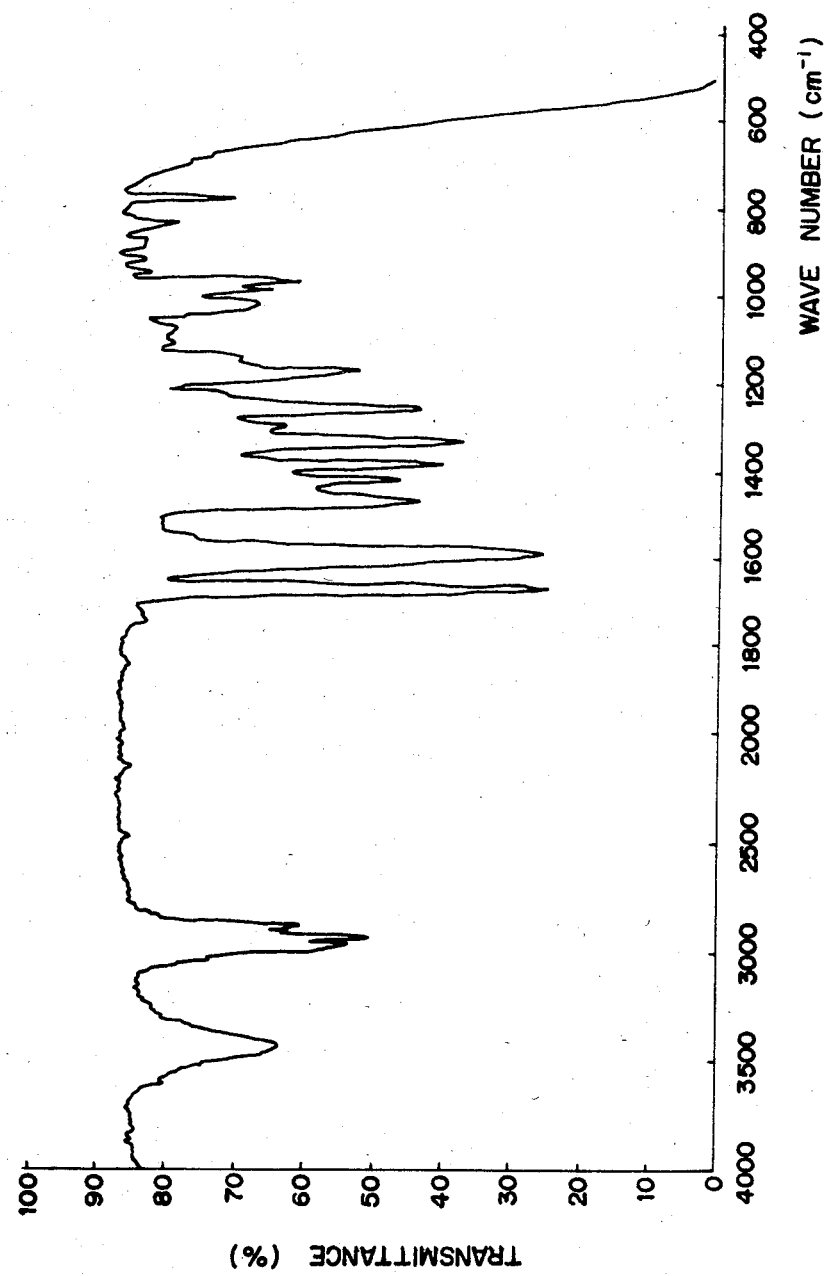
FIG. 2 is an IR absorption spectrum (liquid film method) of physiologically active substance SS 12538A of the present invention.

(7) IR absorption spectrum (Liquid Film Method) See FIG. 2.

(8) $^1$H-NMR spectrum (60 MHz)

Figure 3:
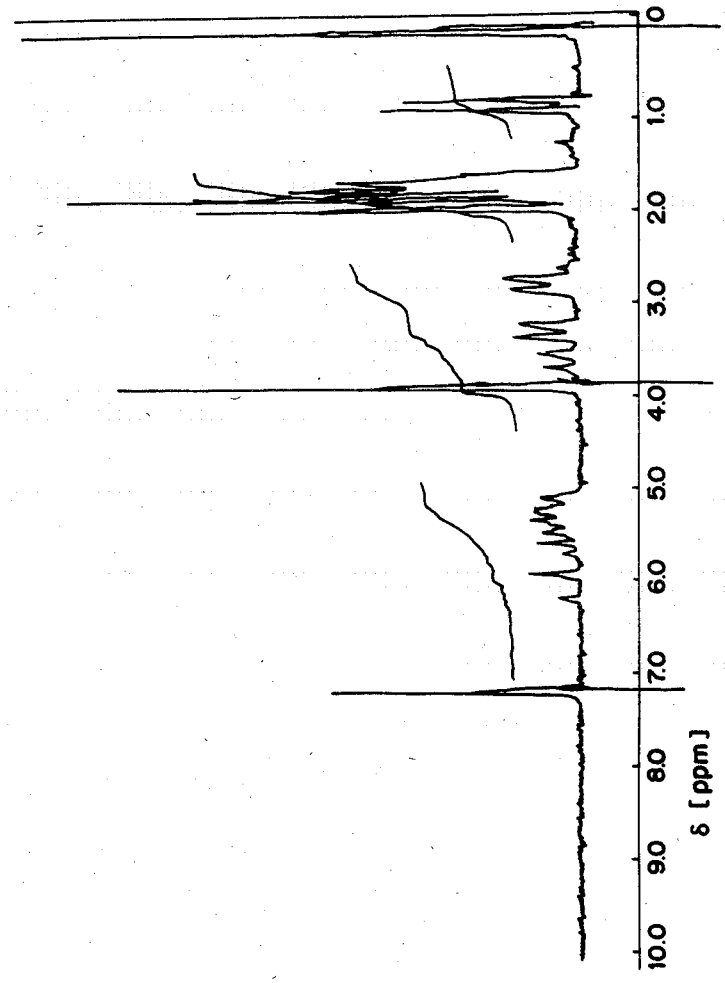
FIG. 3 is a $^1$H-NMR spectrum (solvent: deuterochloroform) of physiologically active substance SS 12538A of the present invention.

Measured in a deuterochloroform solution using TMS as a reference substance. See FIG. 3.

(9) $^{13}$C-NMR spectrum

Measured in a deuterochloroform solution using TMS as a reference substance.

δ(ppm) 181.0, 162.1, 156.8, 138.0, 136.5, 135.9, 135.1, 134.0, 125.0, 122.9, 117.9, 117.8, 99.3, 82.6, 55.1, 42.8, 36.8, 29.9, 17.4, 16.5, 13.0, 13.0, 10.6, 9.8, 6.8.

(10) Molecular formula (by NMR and mass spectrum analyses) $C_{25}H_{36}O_4$.

(11) Structural formula

Based on the above physico-chemical properties, the substance SS 12538A was determined to have a structure of the following formula

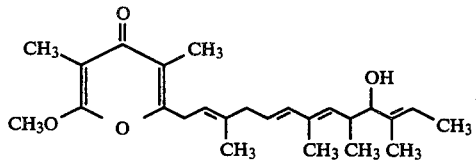

2. Biological Properties (1) Vasodilating activity 4 male mongrel dogs, weighing 15-25 Kg, were provided as laboratory animals and were anesthesized with sodium pentobarbital (30 mg/kg i.v.). Thereafter, the left circumflex coronary artery was exposed under artificial respiration and a probe of an electromagnetic flow meter was attached. A polyethylene cannula was inserted into the left femoral artery.

Test compounds were dissolved in a small amount of dimethyl sulfoxide and diluted with a sterilized physiological saline for injection, followed by dosing it into the vein.

Coronary blood was measured by means of the electromagnetic flow meter and the blood pressure was determined from the polyethylene cannule through a pressure transducer. Also, heart rate was measured by (2) Antibacterial Activity Minimum inhibitory concentration (MIC) of the physiologically active substance SS 12538A against various microorganisms are shown in FIG. 2.

TABLE 2

| Organisms | Minimum Inhibitory Concentration MIC (mcg/ml) |
|---|---|
| Bacillus subtilis ATCC 6633 | >100 |
| Bacillus cereus IID 871 | 12.5 |
| Micrococcus lysodeikticus IFO 3333 | 25 |
| Staphylococcus aureus ATCC 6538P | >100 |
| Staphylococcus epidermidis ATCC 12228 | <6.25 |
| Escherichia coli 0-1 | >100 |
| Klebsiella pneumoniae ATCC 10031 | >100 |
| Pseudomonas aeruginosa IFO 13736 | >100 |
| Candida albicans ATCC 10231 | >100 |
| Saccharomyces cerevisiae ATCC 9763 | >100 |
| Aspergillus niger ATCC 9642 | >100 |
| Trichophyton mentagrophytes QM 248 | >100 |
| Microsporum gypseum IFO 8231 | <6.25 |

II. SS 12538B

1. Physico-chemical Properties (1) Color and nature of substance: colorless oil (2) Molecular weight (from the mass spectrum of an acetate of SS 12538B) 386

(3) Thin layer chromatography

Carrier: silica gel plate F$_{254}$ (by Merck Inc.)

| Developing Solvent Systems | Rf Values |
|---|---|
| Ethyl acetate | 0.29 |
| Benzene/ethyl acetate (1:1) | 0.11 |
| Benzene/acetone (1:1) | 0.13 |

(4) Color reactions

It presents yellow color 2,4-dinitrophenylhydrazine reagent and dark purple color with anisaldehydesulfuric acid. No characteristic colors are obtained with ferric chloride solution.

(5) Solubilities in solvents

Soluble in chloroform, ethyl acetate, acetone, ethyl ether, ethanol, methanol, pyridine, benzene and dimethyl sulfoxide, but sparingly soluble in water.

Figure 4:
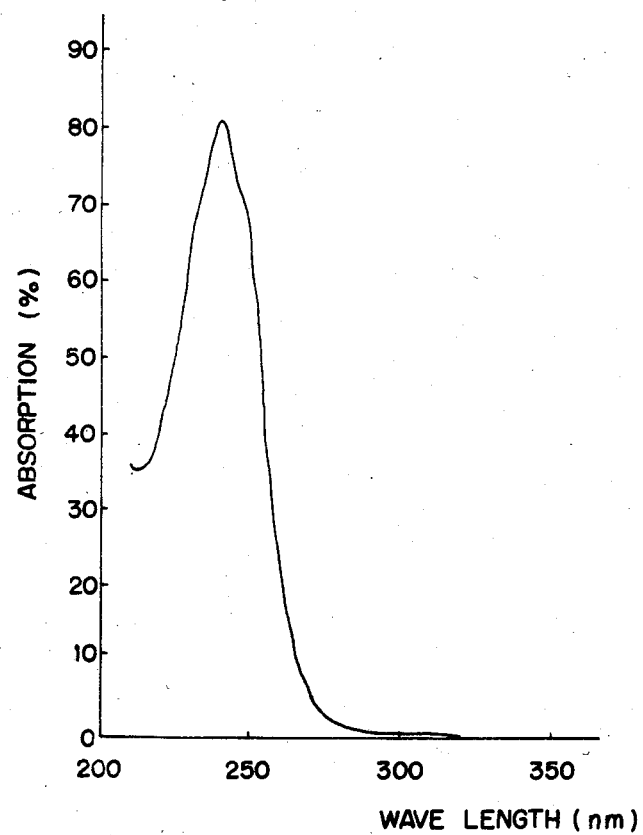
FIG. 4 is an UV absorption spectrum (solvent: methanol) of physiologically active substance SS 12538B of the invention.

(6) UV absorption spectrum $\lambda_{max}^{MeOH} 239$ nm E$_1$ $cm^{1\%} 1010$ (FIG. 4).

Figure 5:
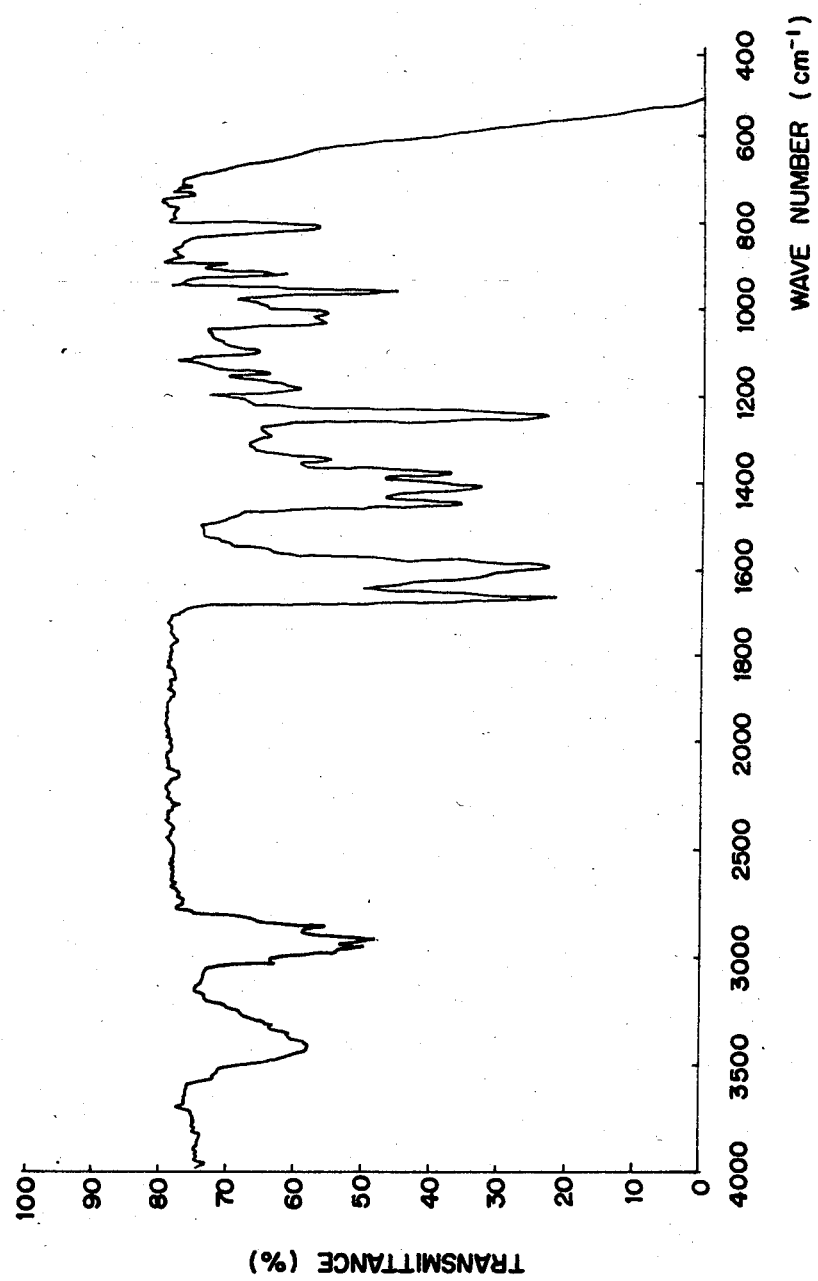
FIG. 5 is an IR absorption spectrum (liquid film method) of physiologically active substance SS 12538B of the invention.

(7) IR absorption spectrum (liquid film method) See FIG. 5.

(8) $^1$H-NMR spectrum (90 MHz)

Figure 6:
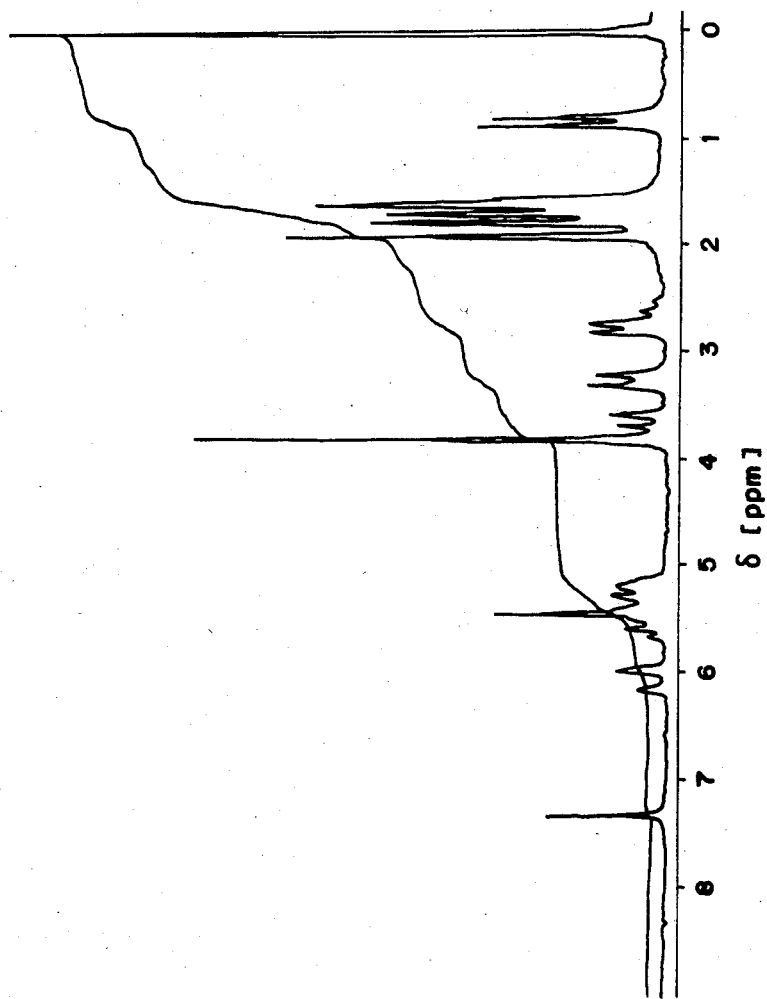
FIG. 6 is a $^1$H-NMR spectrum (solvent: deuterochloroform) of physiologically active substance SS 12538B of the invention.

Measured in a deuterochloroform solution using TMS as a reference substance. See FIG. 6.

(9) $^{13}$C-NMR spectrum

Measured in a deuterochloroform solution using TMS as a reference substance.

δ(ppm) 181.5, 167.2, 159.1, 138.1, 136.4, 135.9, 135.2, 133.9, 125.2, 122.9, 118.4, 117.8, 88.4, 82.6, 55.8, 42.9, 36.8, 30.2, 17.4, 16.5, 13.1, 13.1, 10.6, 9.4.

(10) Molecular formula (from NMR and mass spectra) $C_{24}H_{34}O_4$.

(11) Structural formula

From the values of the above physico-chemical measurements, the substance SS 12538B of the present invention was determined to have a structure of the following formula.

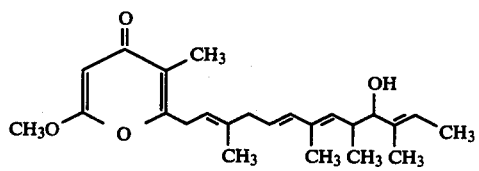

2. Biological Properties (1) Vasodilating activity

In accordance with the procedure as used with SS 12538A, the vasodilating activity of SS 12538B was determined. The results are shown in Table 3 below.

(2) Molecular weight (from mass spectrum of an acetate of SS 12538C) 414

(3) Thin layer chromatography

Carrier: silica gel plate $F_{254}$ (Merck Inc.)

| Developing Solvent Systems | Rf Values |
|---|---|
| Ethyl acetate | 0.77 |
| Benzene/ethyl acetate (1:1) | 0.57 |
| Benzene/acetone (1:1) | 0.44 |

(4) Color reactions

The substance presents yellow color with 2,4-dinitrophenylhydrazine reagent and dark purple color with anisaldehyde-sulfuric acid. No characteristic colors are obtained with ferric chloride solution.

(5) Solubilities in solvents

Soluble in chloroform, ethyl acetate, acetone, ethyl ether, ethanol, methanol, pyridine, benzene and dimethyl sulfoxide but sparingly soluble in water.

Figure 7:
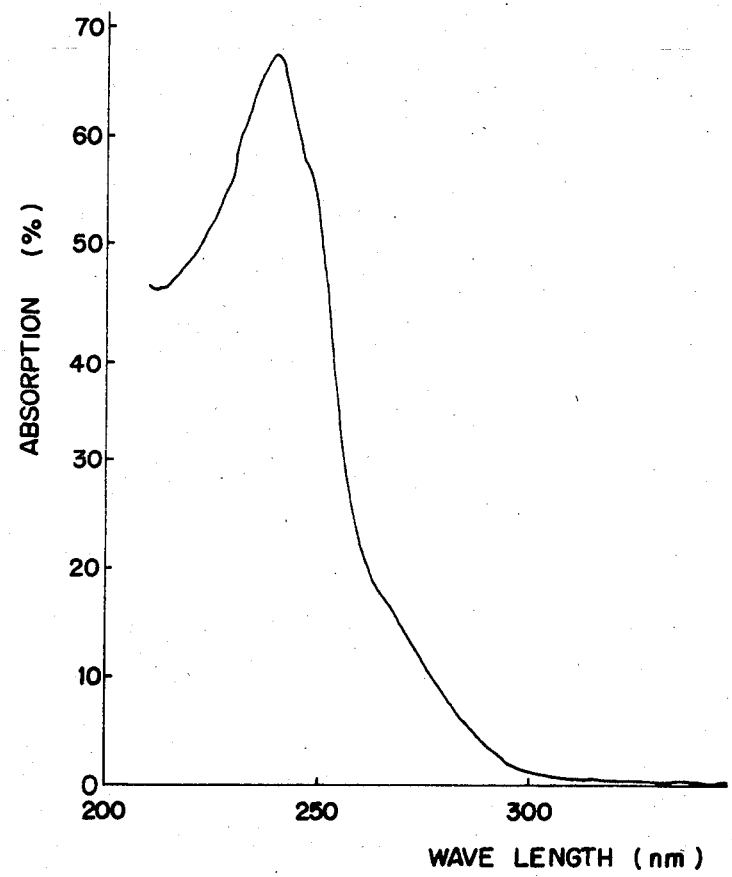
FIG. 7 is an UV absorption spectrum (solvent: methanol) of physiologically active substance SS 12538C of the invention.

(6) UV absorption spectrum $\lambda_{max}^{MeOH}$ 239 nm $E_1 cm^{1\%}$ 840 (FIG. 7).

Figure 8:
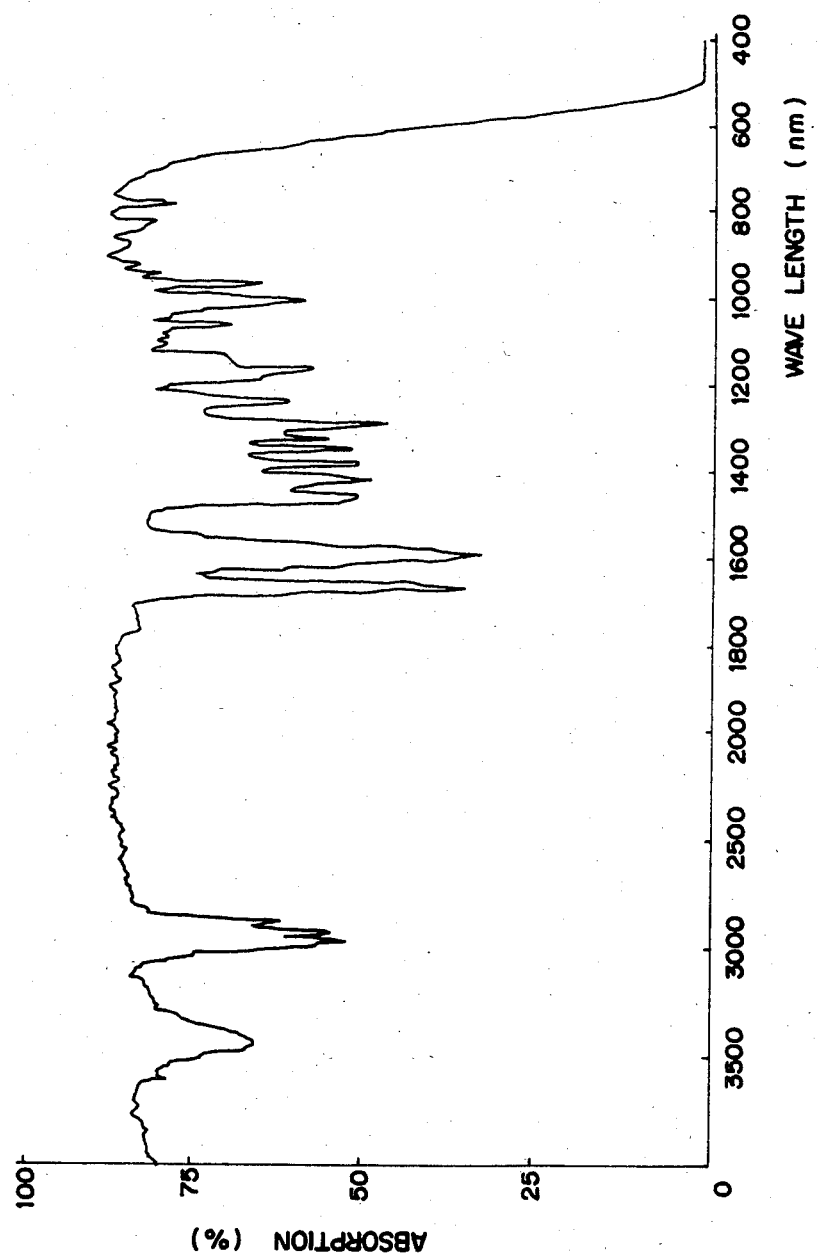
FIG. 8 is an IR absorption spectrum (liquid film method) of physiologically active substance SS 12538C of the invention.

(7) IR absorption spectrum (Liquid Film Method) See FIG. 8.

(8) $^{1}$H-NMR spectrum (90 MHz)

Figure 9:
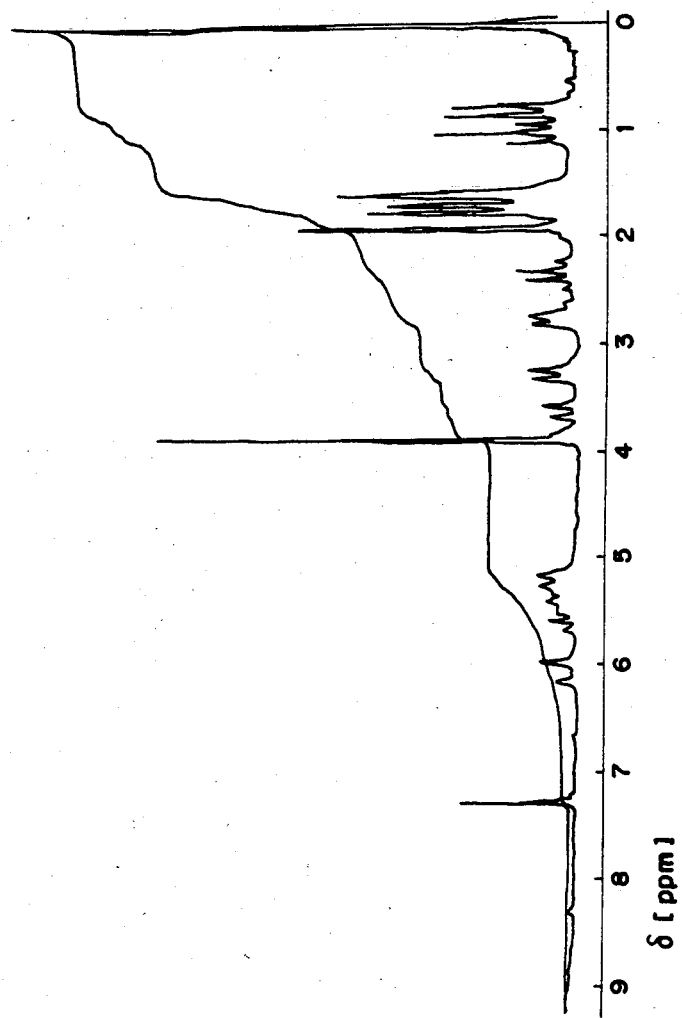
FIG. 9 is a $^1$H-NMR spectrum (solvent: deuterochloroform) of physiologically active substance SS 12538C of the invention.
Figure 10:
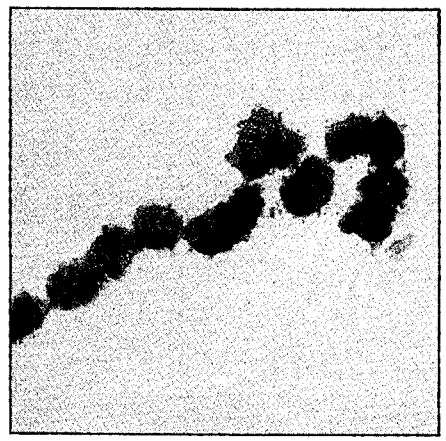
FIG. 10 is an electron microscopic photograph of a microorganism of the invention, Streptomyces pactum S 12538.

Measured in a deuterochloroform solution using TMS as a reference substance. See FIG. 9.

TABLE 3

| Compounds | Dose (μg/kg) | Coronary Blood Flow Increase (%) | Coronary Blood Flow Duration (min) | Blood Pressure Reduction (%) | Blood Pressure Duration (min) | Heart Rate Reduction (%) |
|---|---|---|---|---|---|---|
| SS 12538B | 3.0 | 103.3 | 10 | 7.5 | 6 | 2.0 |
|  | 10.0 | 143.8 | 15 | 27.7 | 20 | 13.0 |
| Dipyridamol | 300.0 | 135.7 | 20 | 13.2 | 16 | 0 |

(2) Antibacterial Activity

Minimum inhibitory concentration (MIC) of the physiologically active substance SS 12538B against various microorganisms are shown in Table 4 below.

TABLE 4

| Organisms | Minimum Inhibitory Concentration MIC (mcg/ml) |
|---|---|
| Bacillus subtilis ATCC 6633 | 50 |
| Bacillus cereus IID 871 | 50 |
| Micrococcus lysodeikticus IFO 3333 | 25 |
| Staphylococcus aureus ATCC 6538P | 25 |
| Staphylococcus epidermidis ATCC 12228 | 25 |
| Escherichia coli 0-1 | >100 |
| Klebsiella pneumoniae ATCC 10031 | >100 |
| Pseudomanas aeruginosa IFO 13736 | >100 |
| Candida albicans ATCC 10231 | >100 |
| Saccharomyces cerevisiae ATCC 9763 | >100 |
| Aspergillus niger ATCC 9642 | >100 |
| Trichophyton mentagrophytes QM 248 | 25 |
| Microsporum gypseum IFO 8231 | 100 |

III. SS 12538C

1. Physico-chemical Properties (1) Color and nature of substance: colorless oil (9) $^{13}$C-NMR spectrum Measured in a deuterochloroform solution using TMS as a reference substance.

(ppm) 180.4, 162.2, 156.9, 138.0, 136.5, 135.8, 135.3, 134.0, 125.3, 123.1, 118.4, 118.0, 105.3, 82.7, 55.2, 42.9, 36.8, 30.1, 17.5, 16.5, 15.3, 13.1, 13.1, 12.9, 10.6, 9.8.

(10) Molecular formula (from NMR and mass spectra) $C_{26}H_{38}O_4$

(11) Structural formula

Based on the above values of the physico-chemical measurements, the substance SS 12538C of the present invention was determined to have a structure of the following formula

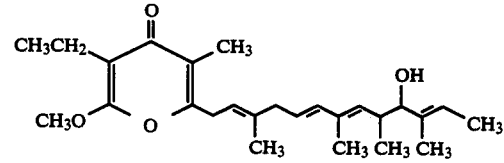

2. Biological Properties (1) Vasodilating activity

In the same manner as in the case of SS 12538A, the vasodilating activity of SS 12538C was determined with the results shown in Table 5.

TABLE 5

| Compounds | Dose (μg/kg) | Coronary Blood Flow | | Blood Pressure | | Heart Rate |
|---|---|---|---|---|---|---|
| | | Increase (%) | Duration (min) | Reduction (%) | Duration (min) | Reduction (%) |
| SS 12538C | 10.0 | 30.0 | 5 | 0 | 0 | 0 |
| | 30.0 | 60.0 | 10 | 2.9 | 10 | 0 |
| | 100.0 | 130.0 | 15 | 8.5 | 15 | 10.1 |
| Di-pyridamol | 300.0 | 135.7 | 20 | 13.2 | 16 | 0 |

(2) Antibacterial activity

Minimum inhibitory concentration (MIC) of the physiologically active substance SS 12538C against various microorganisms are shown in Table 6 below.

TABLE 6

| Organisms | Minimum Inhibitory Concentration MIC (mcg/ml) |
|---|---|
| Bacillus subtilis ATCC 6633 | >100 |
| Bacillus cereus IID 871 | 25 |
| Micrococcus lysodeikticus IFO 3333 | 12.5 |
| Staphylococcus aureus ATCC 6538P | 100 |
| Staphylococcus epidermidis ATCC 12228 | 25 |
| Escherichia coli 0-1 | >100 |
| Klebsiella pneumoniae ATCC 10031 | >100 |
| Pseudomonas aeruginosa IFO 13736 | >100 |
| Candida albicans ATCC 10231 | >100 |
| Saccharomyces cerevisiae ATCC 9763 | >100 |
| Aspergillus niger ATCC 9642 | >100 |
| Trichophyton mentagrophytes QM 248 | 50 |
| Microsporum gypseum IFO 8231 | >100 |

Although those properties of the compounds of the present invention described hereinabove were compared with those of known physiologically active compounds, the compounds of the invention do not correspond to those known ones and are thus considered to be novel physiologically active substance, respectively.

All the physiologically active substances SS 12538 of the present invention exhibit not only the blood pressure depressing action, but also the action of remarkably increasing the flow rate of blood in arteria coronaria. In addition, the substances SS 12538A and SS 12538B have a titer as high as about 30 times currently employed dipyridamol and even with SS 12538C, its titer is as high as about 3 times that of dipyridamol. Accordingly, the substances are considered useful as a curative drug against ischemic heart diseases or a depressant. The physiologically active substances SS 12538 have the antimicrobial activity against a certain Gram-positive bacteria and a certain dermatophytes and are thus useful as an antimicrobial agent.

The present invention is illustrated by way of examples.

EXAMPLE 1

Test of Isolation of Pure Microorganism and Reproducibility:

(1) A collected soil sample was diluted with sterilized water to a level of 1:1000 and 1 ml of the dilution was admixed with 9 ml of an isolation agar medium (I) with the following composition, in a sterilized Petri dish and incubated at 27° C. for several days.

| Isolation agar medium (I) | |
|---|---|
| Oat meal | 20 g |
| (20 g of oat meal was boiled in 1000 ml distilled water for 20 minutes and filtered through a cheese cloth, with a loss of the water being supplemented by adding fresh distilled water.) | |
| Yeast extract | 4 g |
| Glucose | 2 g |
| Trace salts solution | 1 ml |
| $FeSO_4.7H_2O$ | 0.1 g |
| $MnCl_2.4H_2O$ | 0.1 g |
| $ZnSO_4.7H_2O$ | 0.1 g |
| Distilled water | 100 ml |
| Agar | 20 g |
| pH | 7.2 |

Colonies produced by the above cultivation were transferred to a slant agar culture medium (II) by the use of a platinum loop, followed by cultivating at 27° C. for 14 days.

| Slant Agar Medium (II) | |
|---|---|
| Oat meal | 20 g |
| (20 g of oat meal was boiled in 1000 ml distilled water and filtered through cheese cloth, with the resultant loss of the water being supplemented by addition of fresh distilled water.) | |
| Trace salts solution | 1 ml |
| $FeSO_4.7H_2O$ | 0.1 g |
| $MnCl_2.4H_2O$ | 0.1 g |
| $ZnSO_4.7H_2O$ | 0.1 g |
| Distilled water | 100 ml |
| Agar | 18 g |
| pH | 7.2 |

One platinum loop of culture produced on the medium by the cultivation was diluted with a physiological saline solution to 1:10,000. One milliliter was admixed with 9 ml of the isolation agar medium (I) in a sterilized Petri dish and incubated at 27° C. for 14 days. It was visually and microscopically observed that a plurality of the resulting colonies were not different from one another.

Of the plurality of colonies, ten colonies were, respectively, inoculated onto slant agar media (II), followed by cultivating at 27° C. for 14 days. The culture on the ten slant media (II) were confirmed by visual and microscopic observations to be the same culture. In addition, the nature and physiological characteristics of the culture on the ten media were confirmed to be same. The nature and physiological characteristics are just as those discussed hereinbefore.

The test results reveal that the culture on the ten cultured media are all the same culture as that isolated from the natural field.

(2) To the culture on the slant agar medium (II) obtained by the pure culture was added a protecting agent (an aqueous solution containing 10% of skim milk and 1% of sodium glutamate) to prepare a spore suspension on the slant agar medium (II). Aliquots of about 0.5 ml of the spore suspension were in the freeze-drying ampoules and freeze-dried. The freeze-drying was effected by quickly freezing the spore suspension-containing ampoules in dry ice-acetone, setting the ampoules in a freeze dryer, and subjecting the dryer to a vacuum below 0.03 Torr. After sealing in vacua by the use of a gas burner, the freeze-dried culture was stored at 4° C. The thus obtained freeze-dried culture (sample) were preserved for 3 months, after which the ampoules were opened and the culture were transferred to a sterilized test tube using a sterilized mini-spatula. To this tube was added a renaturator (sterilized water), followed by allowing to stand over 1 hour to determine the nature and physiological characteristics of the culture on various media under such conditions as used above. As a result, it was confirmed that those culture were not different from the culture (sample) prior to the lyophilization.

EXAMPLE 2

(i) *Streptomyces pactum* S 12538 (FERM BP-265), i.e. SS 12538-producing culture were inoculated in a medium consisting of 2.0% glycerol, 2.0% dextrine, 1.0% soyton, 0.3% yeast extract, 0.2% ammonium sulfate, and 0.2% calcium carbonate in tap water (pH 7.0), followed by shaking at 27° C. for 48 hours to obtain a seed culture. Thereafter, 15 liters of the production medium having the same composition as that described above was placed in a 30 liter jar fermentor. In the medium was inoculated 300 ml of the seed culture, followed by cultivating under conditions of an aeration rate of 16 /l min, a number of revolutions of 400 r.p.m. and a culture temperature of 27° C. After 96 hours fermentation, the culture broth was centrifuged and the broth supernatant was extracted three times with an equal amount of ethyl acetate. On the other hand, 5 liters of methanol were added to the wet mycelial cake, followed by agitating and filtering. This procedure was repeated two times. The methanol was distilled off from the extract under reduced pressure and the aqueous solution of the residue was extracted three times with each 1 liter of ethyl acetate. The resulting extract was combined with the extract from the broth supernatant, followed by distilling off the solvent under reduced pressure to obtain a mixture of crude SS 12538A, crude SS 12538B and SS 12538C.

(ii) The mixture obtained in (i) was dissolved in a small amount of chloroform and subjected to the column chromatography (column size 3 cm×30 cm) using chloroform and silica gel (by Merck Inc., Kiesel gel 60). First, a fraction containing the crude SS 12538C was eluted, followed by eluting fractions containing the crude SS 12538A and the crude SS 12538B in this order.

(iii) The fraction containing SS 12538C was collected, from which the solvent was distilled off to obtain about 0.6 g of a crudely purified product of light yellow oily SS 12538C. About 0.6 g of this SS 12538C crudely purified product was dissolved in a small amount of benzene/ethyl acetate (4:1) and was subjected to the column chromatography (column size 2 cm×30 cm) using the same solvent and silica gel (Merck Inc., Kiesel Gel 60). The eluted fraction of SS 12538C was collected and the solvent was distilled off to obtain about 0.15 g of the colorless oily substance of a pure SS 12538C.

(iv) The fraction of SS 12538A obtained in (ii) was collected and the solvent was distilled off to obtain about 4 g of a crudely purified SS 12538A product which was light yellow in color and oily. About 4 g of this SS 12538A crudely purified product was dissolved in a small amount of benzene/ethyl acetate (3:1) and was subjected to the column chromatography (column size 2 cm×30 cm) using the same solvent and silica gel (Merck Inc., Kiesel Gel 60). The eluted fraction of SS 12538A was collected and the solvent was distilled off to obtain about 2 g of the colorless oily substance of pure SS 12538A.

(v) The SS 12538B fraction obtained in (ii) was collected and the solvent was distilled off to obtain about 0.5 g of a crudely purified product of light yellow oily SS 12538B. About 0.5 g of the SS 12538B crudely purified product was dissolved in a small amount of benzene/ethyl acetate (1:1) and was subject to the column chromatography (column size 2 cm×30 cm) using the same solvent and silica gel (Merck Inc., Kiesel Gel 60). The eluted fraction of SS 12538B was collected and the solvent was distilled off to obtain about 0.12 g of the colorless oily substance of pure SS 12538B.

What is claimed is:

1. A physiologically active substance SS 12538 of the following general formula (I)

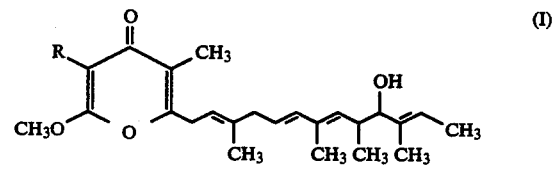

in which R represents a hydrogen atom, a methyl group or an ethyl group.

2. The substnce of claim 1 wherein R represents a hydrogen atom.

3. The substance of claim 1, wherein R represents a methyl group.

4. The substance of claim 1, wherein R represents an ethyl group.

* * * * *